(12) United States Patent
Sibeijn et al.

(10) Patent No.: US 6,812,001 B2
(45) Date of Patent: Nov. 2, 2004

(54) ISOLATION OF CAROTENOID CRYSTALS FROM MICROBIAL BIOMASS

(75) Inventors: Mieke Sibeijn, Amersfoort (NL); Robertus Mattheus De Pater, Delft (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 10/029,316

(22) Filed: Dec. 20, 2001

(65) Prior Publication Data

US 2002/0055135 A1 May 9, 2002

Related U.S. Application Data

(63) Continuation of application No. 09/402,604, filed on Oct. 22, 1999, now abandoned.

(30) Foreign Application Priority Data

May 2, 1997 (EP) .............................. 97201306

(51) Int. Cl.⁷ ......................... C12P 23/00; C07C 403/00
(52) U.S. Cl. ......................... 435/67; 435/171; 585/351; 585/803; 585/836
(58) Field of Search .................. 435/67, 171; 585/351, 585/803, 836

(56) References Cited

U.S. PATENT DOCUMENTS

| | | | |
|---|---|---|---|
| 3,226,302 A | * 12/1965 | Ciegler | ......................... 435/67 |
| 3,268,606 A | * 8/1966 | Jaeger et al. | .................. 435/67 |
| 3,356,753 A | * 12/1967 | Sarnecki | ...................... 435/67 |
| 3,492,202 A | * 1/1970 | Bohinski | ...................... 435/67 |
| 5,378,369 A | * 1/1995 | Rose et al. | .................. 210/637 |

FOREIGN PATENT DOCUMENTS

| GB | 1 064 645 | 4/1967 |
|---|---|---|
| WO | WO 98 03480 | 1/1998 |

OTHER PUBLICATIONS

Database WPI, Section Ch, Week 9526, Derwent Publications Ltd., London, GB, AN 95–194788, XP002043884.
Gallik et al., *Isolation of Crystals from Phycomyces–Blakes Ecanus*, Biophys. Soc. Annu. Meet. Abstr. 14 (1970) 57A, XP002043881.
Kudinova et al., *Kinetics of Beta Carotene Accumulation During the Fermentation of Blakeslea–Trispora*, Biol. Abstr. 94 (1992) Abstract No. 130801, XP002076403.
Ootaki et al., *Octahedral Crystals in Phycomyces*, J. Cell. Biol. 57(2):278–88 (1973) XP002043880.
Yuan et al., *Method for Separation of Natural Antitumor Cis– and Trans– Beta– Carotene Isomer*, Chem. Abstr. 120(22) (1994) Abstract No. 280268, XP002076404.

* cited by examiner

*Primary Examiner*—Francisco Prats
(74) *Attorney, Agent, or Firm*—Morrison & Foerster LLP

(57) ABSTRACT

A process for the isolation of crystalline carotenoid compound from microbial biomass comprising disrupting the microbial cell walls, separating cellular debris from the carotenoid-containing residue, washing one member of the group consisting of the microbial biomass, the disrupted cell mass and the carotenoid-containing reside with a solvent to remove lipid, suspending the obtained carotenoid crystals in water to float the crystals, recovering the crystals and, optionally, further purifying the crystals which avoids the use of large amounts of solvent of carotenoid extraction process.

14 Claims, No Drawings

ISOLATION OF CAROTENOID CRYSTALS FROM MICROBIAL BIOMASS

This application is a continuation of application Ser. No. 09/402,604, field Oct. 22, 1999, now abandoned, which is a 371 of PCT/EP98/02782, field Apr. 29, 1998.

FIELD OF THE INVENTION

The present invention relates to the field of microbially produced carotenoid compounds.

BACKGROUND OF THE INVENTION

Currently, β-carotene crystals with a high purity (96% or higher) are produced by chemical synthesis. When derived from a natural source, β-carotene mostly is in the form of an oily extract (palm oil, algal oil). Although it is also possible to obtain β-carotene crystals from natural sources, such as vegetables (for example carrots) or micro-organisms (for example algae (Dunaliella) or fungi (Blakeslea), the currently available processes to obtain relatively pure crystals from said natural sources have important disadvantages.

Purification of β-carotene crystals from natural sources comprises extraction of the β-carotene from said source with a suitable extractant, optionally followed by additional purification steps until the desired purity is obtained.

The extraction is carried out with various extractants: organic solvents, such as ethyl acetate, butyl acetate, hexane; vegetable oils, or supercritical fluids, such as propane, ethylene, $CO_2$. Subsequently, the β-carotene crystals can be directly crystallized from the extract obtained after solvent extraction of said natural source, e.g. by evaporation of the solvent.

A main disadvantage of a solvent extraction process is that the β-carotene crystals should firstly be solubilized in a solvent, whereupon, after separating the biomass residue from the β-carotene-containing solvent, the β-carotene should be crystallized again. In addition, a considerable loss of β-carotene can easily occur.

To circumvent the use of the large amounts of solvent which are necessary to solubilize the β-carotene, it would be desirable to directly isolate β-carotene, or any other carotenoid, in a crystalline form from microbial biomass.

DESCRIPTION OF THE INVENTION

The present invention describes a process for the isolation of a carotenoid compound from microbial biomass. The process of the invention is applicable to microbial biomass in which carotenoid compounds are present in a crystalline form. According to the process of the present invention, the carotenoid crystals are directly separated from the microbial biomass. An important advantage of the process of the invention is that it is applicable without using large amounts of solvent. In particular, the amount of solvent used in the process of the invention is substantially reduced as compared to the large amounts of solvent which are needed to solubilize the carotenoid using a conventional solvent-extraction process.

The process of the invention essentially comprises the steps of disrupting the microbial cell walls, separating cellular debris from the carotenoid-containing residue, including a wash of either the microbial biomass, the disrupted cell mass or the carotenoid-containing residue with a solvent suitable to remove lipid, floating the obtained carotenoid crystals in water, and optionally, further purifying the crystals.

The following steps of the process of the invention are described in more detail.

The carotenoid-containing microorganism can be a bacterial, a yeast, a fungal or an algal microorganism. Preferably, the carotenoid-containing microorganism is a yeast, a fungus or an algae. More preferably, it is a yeast of the genus *Phaffia*, a fungus of the order *Mucorales* or an algae of the genus *Dunaliella*.

Microbial carotenoid-containing biomass is obtained from any suitable fermentation of a carotenoid-producing microorganism of choice, as specified above.

The microbial biomass which is subjected to the process of the invention may be in the form of a wet cell cake or in a dry form. For economical reasons, the use of a wet cell cake is preferred. Dry biomass may for instance be in the form of an extrudate, as is described in WO 97/36996.

Cell disruption may occur via methods known in the art. The disruption may occur physically (mechanically), enzymatically and/or chemically. Preferably, cell disruption is performed by mechanical means. Mechanical disruption may occur for instance by homogenizing microbial biomass in a homogenizer under high pressure or using a bead mill or by ultrasonification. Chemical disruption may occur in a low or high pH environment, or by addition of a solvent such as octanol. Enzymatical disruption may occur by action of an enzyme or enzyme mixture degrading constituents of the microbial cell wall.

For efficient cell disruption, the biomass typically may have a dry matter content of about 10 to about 200 g/l. Conveniently, the fermentation broth directly obtained after fermentation is used, having a dry matter content of about 50 g/l. When the starting material is dry biomass, said biomass is mixed with a sufficient amount of water to obtain a dry matter content of about 10 to about 200 g/l, as specified above.

To improve the yield of the recovery process of the invention, an organic solvent not miscible with water may optionally be added to the disrupted cell mass before any further processing steps are taken. Depending on the type of disruption process being applied, addition of said solvent comprises an addition occurring before, during or after cell disruption. For instance, in the case that the cells are disrupted by homogenizing, the solvent preferably is added after the disruption step. The oil or the solvent is added in an amount of 1% to 100% of the amount of biomass suspension or disrupted cell mass, preferably 3% to 10% of the amount of biomass suspension or disrupted cell mass. A suitable organic solvent not miscible with water is, for instance, an oil, hexane or ethyl acetate. Preferably, an oil is added to the disrupted cell mass. Examples of suitable oils are vegetable oils such as soybean oil.

From the resulting disrupted cell mass, a substantial part of the cellular debris is removed by decantation or centrifugation. Preferably, a centrifugation step is applied. Said centrifugation results in a solid upper, a liquid middle and a solid under layer, the solid upper layer containing the carotenoid crystals, also called the carotenoid-containing residue. Only a very small amount of carotenoid is lost in this step.

Optionally, the solid upper layer with the carotenoid-containing residue, said residue essentially consisting of carotenoid crystals, microbial lipid and remaining cellular debris, is washed with water one or more times, to remove additional cellular debris. Said water optionally may contain a salt, such as sodium chloride. The salt may be present in a concentration up to 25% (w/w).

The process of the invention further includes a washing step with a suitable solvent to remove a substantial part of the microbial lipid and, optionally, any oil previously added to the disrupted cells.

A suitable solvent for lipid removal is a lipid- and water-miscible solvent in which the crystalline carotenoid has a low solubility. Preferably, said solvent is a lower alcohol, such as methanol, ethanol, isopropanol, or acetone. More preferably, said solvent is ethanol. It should be noted that the amount of solvent necessary for lipid removal is substantially lower than the amount of solvent necessary for solvent-extraction of a carotenoid from microbial biomass.

In a preferred embodiment of the invention, the carotenoid-containing residue obtained after separation of the cellular debris is washed with said suitable solvent for lipid removal. Said washing is carried out by stirring the carotenoid-containing residue for a convenient time period, e.g for about 10 minutes, with said solvent and recovering the solid under layer after centrifugation. Optionally, said washing with said solvent is repeated one or more times.

In another embodiment of the invention, lipid can be removed from the microbial biomass before cell disruption takes place. This alternative embodiment especially is applicable if the starting biomass material is in a dry form. Typically, dry biomass is suspended in the solvent of choice in an amount of 10 to 400 g biomass per liter solvent. To increase the amount of lipid which is removed, an elevated temperature, e.g. 50° C., may be applied. The thus treated biomass is separated from the lipid-containing solvent by filtration or centrifugation. Optionally, the treatment is repeated.

Washing, as referred to in this invention, includes a step of suspending or stirring the material to be washed in a suitable amount of the solvent of choice and a step of decantation or centrifugation and subsequent recovery of the appropriate layer.

The crystals obtained after cellular debris and lipid removal are subsequently suspended in water, causing the carotenoid crystals to float. Floating of the crystals is improved by bubbling of gas through the suspension. Typically, in a batchwise operation, gas bubbling is continued until the under layer is substantially decolorized. The gas which is used is not critical and may, for instance, be air or nitrogen. Following this floating step, the crystals are recovered by centrifugation or decantation. In this way, the crystals, being present in the upper layer, are separated from any remaining cellular debris, being present in the lower layer, by an intermediate liquid layer.

Floating of the crystals may be improved in the presence of a salt or an oil in the water used for suspending the crude crystals. Therefore, the water optionally may contain a salt, such as sodium chloride, and/or a vegetable oil, such as soybean oil. The salt may be present in a concentration of up to 25% (w/w), the oil in a concentration of up to 2%. Preferably, an oil is present in the water wherein the carotenoid crystals are suspended.

The crude crystals obtained after the solvent washing(s) and floating of the crystals in water are either dried or are further purified to the desired purity level.

Additional purification steps may comprise additional washing steps with a suitable solvent. For instance, a further treatment of the crystals is advantageously carried out using a solvent in which the crystalline carotenoid has a low solubility. Said solvent treatment comprises the steps of stirring the crude carotenoid crystals in said solvent during a time period sufficient to enable dissolution of impurities, filtering off the crystals and washing the crystals several times with fresh solvent. Said stirring can be performed at any desired temperature within a range of about 20 to 80° C. When stirring is performed at a relatively elevated temperature, the mixture preferably is cooled before filtering off the crystals.

Optionally, this treatment is repeated one or more times, whereby the treatment can be repeated with the same or with a different solvent than the first solvent used. After the final washing step, residual solvent is evaporated.

Suitable solvents for further purification are solvents in which the carotenoid has a low solubility, i.e. a solubility of at most 1 g/l at 25° C. Preferably, the solvent is water or an organic solvent. When water is used, the pH of the water is not a critical factor for the treatment, although it is preferred that the pH is below 7. More preferably, the pH of the water is 4–6. The organic solvent preferably is a lower alcohol or lower acyl ester thereof, wherein lower is understood to comprise 1 to 5 carbon atoms, or acetone. More preferably, the organic solvent is ethanol or ethylacetate.

The process of the present invention is advantageously applied to any microorganism in which a carotenoid compound is present in a predominantly crystalline form. Preferably, the process of the invention is carried out using a microorganism containing a carotenoid which is for at least 50% in a crystalline form, more preferably which is for at least 60% and most preferably which is for at least 70% in a crystalline form.

Because of their low solubility in a cellular environment, especially apolar carotenoids are present in a predominantly crystalline form within the cell. Examples of apolar carotenoid compounds are phytoene, present in for instance certain *Phaffia rhodozyma* strains, or β-carotene, present in for instance *Blakeslea trispora* or *Phycomyces blakesleanus*.

The carotenoid crystals obtained when applying the process of the invention have a high purity and are advantageously used in food, pharmaceutical or cosmetic compositions.

EXAMPLE 1

Direct Isolation of β-carotene Crystals from *Blakeslea Trispora*

2.0 l of fermentation broth of *Blakeslea trispora* containing 0.164% (w/w) of β-carotene was homogenized twice at a pressure of 800–1000 bar. After centrifugation of the mixture, the upper layer was mixed with 750 ml of demineralized water. The mixture was centrifuged and the upper layer was mixed with 750 ml of demineralized water again. After centrifugation of the mixture, the upper layer was stirred with 750 ml of ethanol for 5 minutes. After centrifugation the upper layer was decanted. The under layer was successively washed four times with ethanol (as written before) and stirred with 700 ml of demineralized water (stage 1) for 10 minutes, causing the crystals to float. The crystals obtained after centrifugation were dried under vacuum.

EXAMPLE 2

Floating in the Presence of Salt or Oil

Instead of demineralized water, either salt water (25% (w/w) sodium chloride in water) or water containing soybean oil (1%) was added at stage 1. In this way, a higher overall β-carotene yield was obtained.

EXAMPLE 3

Further Purification of β-carotene Crystals

An amount of 7 g of the crystal suspension obtained after the final centrifugation step (see Example 1) was mixed once with 45 ml of demineralized water. After centrifugation 300 ml of ethanol was added to the upper layer and the mixture was mixed and centrifuged. The upper layer was decanted and 300 ml of ethanol was mixed with the under layer. Again the upper layer was decanted, after which the under layer (crystal slurry) was stirred with 20 ml of ethyl acetate at 50° C. under nitrogen for 30 minutes. The suspension was cooled to 5° C. in 30 minutes. The crystals were successively filtered off, washed twice with 5 ml of ethyl acetate of 5° C., and stirred with 20 ml of ethanol at 50° C. under nitrogen for 30 minutes. The suspension was cooled to 20° C. in 30 minutes. The crystals were filtered off, washed twice with 5 ml of ethanol, and dried under vacuum at room temperature, giving 1.22 g of β-carotene with a purity of 93.9% according to HPLC (92.8% of trans β-carotene and 1.1% of 13-cis β-carotene). The overall yield was 35%.

What is claimed is:

1. A process for the direct isolation of crystalline carotenoid compound from microbial biomass without a carotenoid solubilization step, the process comprising disrupting the microbial cell walls, separating cellular debris from the resulting carotenoid crystal containing residue, washing the carotenoid crystal containing residue with a solvent to remove lipid, suspending the obtained carotenoid crystals in water to float the crystals and re ye biomass debris, and recovering the crystals.

2. The process of claim 1, wherein the carotenoid crystal containing residue is washed with water prior to lipid removal.

3. The process of claim 1, wherein the solvent to remove lipid is a lower alcohol or acetone.

4. The process of claim 1, wherein a solvent immiscible with water is added to the microbial cells before, during or after disrupting the cell walls.

5. The process of claim 4, wherein said solvent immiscible with water is added to the disrupted cell mass after disrupting the cell walls.

6. The process of claim 4, wherein said solvent immiscible with water is an oil.

7. The process of claim 1, wherein floating of the crystals is effected with bubbling of a gas through the suspension.

8. The process of claim 1, wherein the water to float the crystals further contains a salt and/or an oil.

9. The process of claim 8, wherein the water to float the crystals contains a vegetable oil.

10. The process of claim 1, wherein the microbial biomass is from *Blakeslea trispora*.

11. The process of claim 1, wherein the carotenoid compound is β-carotene.

12. The process of claim 3, wherein the solvent is ethanol.

13. The process of claim 6, wherein the oil is a vegetable oil.

14. The process of claim 1, wherein the recovered crystals are further purified.

* * * * *